United States Patent [19]

Kathawala

[11] 4,064,273
[45] Dec. 20, 1977

[54] TREATING LIPIDEMIA WITH SUBSTITUTED DIPHENYL ETHER HALIDES AND COMPOSITIONS THEREOF

[75] Inventor: Faizulla G. Kathawala, West Orange, N.J.

[73] Assignee: Sandoz, Inc., E. Hanover, N.J.

[21] Appl. No.: 649,715

[22] Filed: Jan. 16, 1976

Related U.S. Application Data

[62] Division of Ser. No. 520,361, Nov. 4, 1974, abandoned.

[51] Int. Cl.$^2$ ............................................. A61K 31/085
[52] U.S. Cl. ...................................................... 424/340
[58] Field of Search .......................................... 424/340

[56] References Cited

U.S. PATENT DOCUMENTS 2,170,989  8/1939  Coleman et al. .................. 260/612 R Primary Examiner—Albert T. Meyers
Assistant Examiner—Daren M. Stephens
Attorney, Agent, or Firm—Gerald D. Sharkin; Richard E. Vila; Joseph J. Borovian

[57] ABSTRACT

Hypolipidemic agents of the formula:

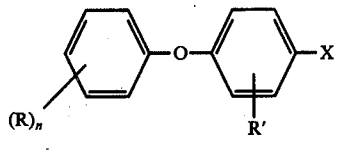

wherein
  R is branched lower alkyl,
  R' is hydrogen or alkyl,
  X is halo, and
  n is 2.

9 Claims, No Drawings

TREATING LIPIDEMIA WITH SUBSTITUTED DIPHENYL ETHER HALIDES AND COMPOSITIONS THEREOF

This is a division of application Ser. No. 520,361 filed Nov. 4, 1974, now abandoned.

The present invention relates to substituted diphenyl ether halides, e.g., 1-(3,5-di-tertiary butylphenoxy)-4-bromobenzene, and to their use as hypolipidemics. The invention also relates to pharmaceutical compositions containing the above compounds as an active ingredient thereof and to the method of using such compositions for the treatment of lipidemia.

The compounds with which this invention is concerned may be represented by the following structural formula:

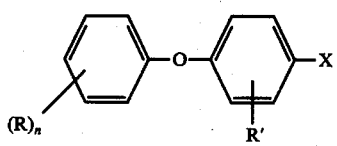

wherein
R is branched alkyl of 3 to 5 carbon atoms, preferably tertiary branched alkyl, e.g., t-butyl,
R' is hydrogen or alkyl of 1 to 4 carbon atoms,
X is halo of atomic weight of from 18 to 80, and
n is 2,
with the proviso that the R groups are not in ortho position with respect to each other.

The compounds of formula (I) may be prepared by the following reaction scheme:

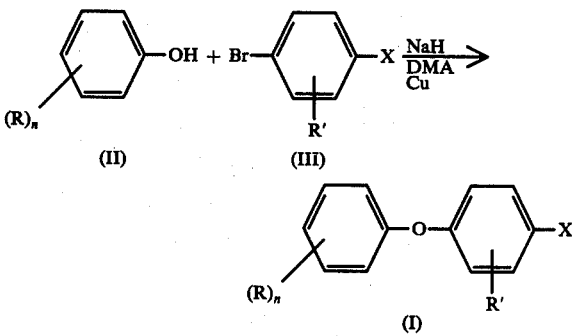

wherein R, R', X and n are as defined above.

This process is conducted by reacting (II) with (III) in the presence of an inorganic base, an inert organic solvent and a small amount of copper metal at temperatures in the range of 100° C. to 180° C., preferably at the reflux temperature of the system, for a period of time between 4 and 24 hours. Suitable inorganic bases include alkali metal hydroxides, e.g., sodium hydroxide, potassium hydroxide and the like, or sodium hydride, the latter being especially preferred. The reaction is carried out in the presence of an inert organic solvent such as lower alkanols, e.g., methanol, ethanol and the like, dimethyl formamide, dimethyl acetamide or acetonitrile, preferably dimethyl acetamide.

The compounds (I) are also preparable by the following reaction scheme:

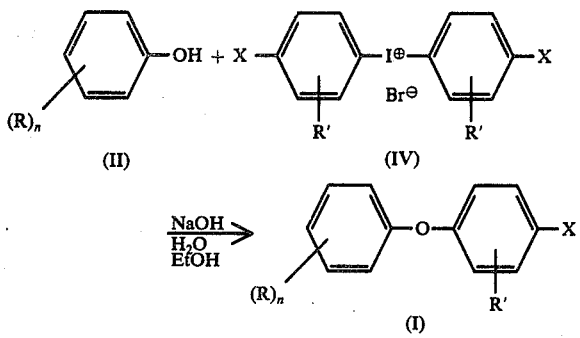

wherein R, R', X and n are as defined above. This process is conducted by reacting (II) with (IV) in the presence of an inorganic base, an inert organic solvent and water at temperatures in the range of 50° C. to 100° C., preferably at the reflux temperature of the system, for a period of time between 4 and 24 hours. Suitable inorganic bases and inert, organic solvents include those as earlier described with reference to the preparation of compounds (I) from compounds (II) and (III), a preferred inorganic base being sodium hydroxide and a preferred inert, organic solvent being ethanol.

The compounds of formula (I) may be recovered using conventional techniques such as crystallization, filtration or column chromatography.

Certain of the compounds of the formulae (II), (III), and (IV) are known and may be prepared by methods disclosed in the literature. Those compounds not specifically disclosed may be prepared by analagous methods from known starting materials.

As previously indicated, the compounds of formula (I) are useful because they possess pharmacological activity in animals, e.g., mammals. In particular, the compounds of formula (I) are useful as hypolipidemic agents in the treatment of lipidemia, in particular, hyperlipoproteinemia as indicated by the fall in cholesterol and/or triglyceride levels in male albino Wistar rats weighing 110-130 g. initially. The rats are maintained on drug-free laboratory chow diet for seven days and then divided into groups of 8 to 10 animals. Each group with the exception of the control is then given the compound orally at a dose of 7.5, 30, 250, or 500 milligrams per kilogram of body weight per day, p.o. for 6 days. At the end of this period, the animals are anesthetized with sodium hexobarbital and bled from the carotid arteries. Serum or plasma samples are then extracted with isopropanol, and the cholesterol content of the extracts is estimated on a Technicon Autoanalyzer by standard methodology. For example, 1.0 ml. of serum is added to 9.0 ml. redistilled isopropanol. Two autoanalyzer cupsful of a mixture of zeolite-copper hydroxide and Lloydds reagent (Kessler, G., and Lederer, H., 1965, Technicon Symposium, Mediad Inc., New York, 345-347) are added; and the mixture is shaken for 1 hour. Cholesterol levels are determined using this sample by the standard Technicon N 24A (cholesterol) methodology. The mean total serum cholesterol levels are then computed and the hypocholesterolemic activity is expressed as the fall in cholesterol levels as a percentage of the control level. For the triglyceride determination, blood samples are collected as above and 1.0 ml. samples of the serum are added to 9.0 ml. redistilled isopropanol. Two autoanalyzer cupsful of a mixture of zeolite-copper hydroxide and Lloydds reagent (Kessler, G., and Lederer, H., 1965, Technicon Symposium, Mediad Inc., New York, 345–347) are added; and the mixture is shaken for 1 hour. After centrifugation, 2 ml. of the clear supernates are evaporated to dryness and saponified by addition of 0.1 ml. 10% KOH in 90% ethanol and 1.0 ml. Skelly B (petroleum ether b.p. 60°–70° C.). After acidification and the removal of fatty acids with petroleum ether, the aqueous phases are neutralized, suitably diluted with water, and analyzed for glycerol by the method of Lofland (Anal. Biochem. 9, 393, 1964) using the Technicon Autoanalyzer. The change in serum triglyceride levels induced by the drug is computed as a percentage of the control triglyceride levels.

For such usage, the compounds may be administered orally or parenterally, preferably orally, and in admixture with conventional pharmaceutical carriers. The anti-hyperlipidemic effective dosage of the compounds of formula I employed for the alleviation of lipidemia may vary depending on the particular compound employed and the severity of the condition being treated. In general, satisfactory results are obtained when administered at a daily dosage of from about 10 milligrams to about 250 milligrams per kilogram of animal body weight, preferably given orally and in divided doses, 2 to 4 times a day, or in sustained release form. For most mammals, the total daily dosage is from about 600 milligrams to about 4000 milligrams of the compound, and dosage forms suitable for internal administration comprise from about 150 to 2000 milligrams of the compound in admixture with a solid or liquid pharmaceutically acceptable carrier or diluent.

For above usage, the compounds of formula I may be administered orally in such forms as tablets, dispersible powders, granules, capsules, syrups and elixirs; and parenterally as solutions, suspensions, dispersions, emulsions, and the like, e.g., a sterile injectable solution such as an aqueous suspension. These pharmaceutical preparations may contain 0.5% up to about 90% of the active ingredient in combination with the carrier or adjuvant, more usually between 3% and 50% by weight. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium phosphate, calcium sulphate dihydrate, lactose and talc, granulating and disintegrating agents, e.g., starch and alginic acid, binding agents, e.g., starch, gelatin, polyvinyl pyrrolidone and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert liquid or solid diluent, e.g., calcium carbonate, calcuim phosphate, kaolin, peanut oil, sesame oil and corn oil. The preferred pharmaceutical compositions from the standpoint of preparation and ease of administration are solid compositions, particularly hard-filled capsules and tablets.

Capsules containing the ingredients indicated below may be prepared by conventional techniques and are useful in treating lipidemia, particularly hyperlipoproteinemia, in mammals at a dose of one capsule, 2 to 4 times a day.

| Ingredients | Weight (mg.) |
| --- | --- |
| 1-(3,5-di-tertiary butylphenoxy)-4-bromobenzene | 300 |
| kaolin | 300 |
| Total | 600 mg. |

The following examples are merely illustrative of specific compounds of the invention and the manner in which they may be prepared.

EXAMPLE 1

1-(3,5-di-tertiary butylphenoxy)-4-bromobenzene

To a suspension of 8.8 g. of 50% sodium hydride (mineral oil dispersion) in 320 ml. of dry dimethylacetamide is added, in portions over 15 minutes with vigorous stirring, 32 g. of 3,5-di-tertiary butylphenol, during which the reaction mixture is cooled with an icebath to moderate the internal temperature. The reaction mixture is then stirred at room temperature for 1 hour, after which is added 75.2 g. of dibromobenzene and 800 mg. of copper powder. The resultant mixture is refluxed for 8 hours, after which time it is cooled and the dimethylacetamide is removed in vacuo. The resultant residue is extracted several times with methylene chloride and the insoluble copper filtered off. The combined methylene chloride extracts are washed two times with water, dried over sodium sulfate, filtered, evaporated in vacuo to dryness and the residue recrystallized from ethanol to obtain 1-(3,5-di-tertiary butylphenoxy)-4-bromobenzene, m.p. 98°–100° C.

EXAMPLE 2

Following essentially the procedure of Example 1, and using in place of dibromobenzene, an equivalent amount of:
  a. p-chlorobromobenzene,
  b. p-fluorobromobenzene, and
  c. 4-bromo-5-methylbromobenzene,
there is obtained
  a. 1-(3,5-di-tertiary butylphenoxy)-4-chlorobenzene,
  b. 1-(3,5-di-tertiary butylphenoxy)-4-fluorobenzene, and
  c. 1-(3,5-di-tertiary butyphenoxy)-4-bromo-5-methylbenzene, respectively.

EXAMPLE 3

1-(3,5-di-tertiary butylphenoxy)-4-bromobenzene

To a solution of 7.2 g. of sodium hydroxide in 1300 ml. of water and 300 ml. of ethanol is added successively 37 g. of 3,5-di-tertiary butylphenol and 83 g. of 4,4'-dibromodiphenyl-iodinium bromide. The reaction mixture is refluxed for 16 hours, after which time the ethanol is removed in vacuo and the aqueous layer is decanted off from the crystalline material. The residue is extracted several times with ether and the combined extracts are washed several times with 2N sodium hydroxide, then with water, dried over anhydrous sodium sulfate, filtered, evaporated in vacuo to dryness and the resultant residue recrystallized from ethanol to obtain 1-(3,5-di-tertiary butylphenoxy)-4-bromobenzene, m.p. 98°–100° C.

EXAMPLE 4

Following essentially the procedure of Example 3, and using in place of 4,4'-dibromodiphenyl-iodinium bromide, an equivalent amount of:

a. 4,4'-dichlorodiphenyl-iodinium bromide, and b. 4,4'-difluorodiphenyl-iodinium bromide, there is obtained a. 1-(3,5-di-tertiary butylphenoxy)-4-chlorobenzene, and b. 1-(3,5-di-tertiary butylphenoxy)-4-fluorobenzene, respectively.

What is claimed is:

1. A pharmaceutical composition in unit dosage form for treating lipidemia in mammals comprising an inert pharmaceutically acceptable carrier and from 150 to 2000 milligrams of a compound of the formula:

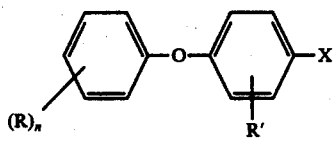

wherein

R is branched alkyl of 3 to 5 carbon atoms,

R' is hydrogen or alkyl of 1 to 4 carbon atoms,

X is halo of atomic weight of from 18 to 80, and $n$ is 2, with the proviso that the R groups are not in ortho position with respect to each other.

2. A composition in accordance with claim 1 in which the compound is of the formula:

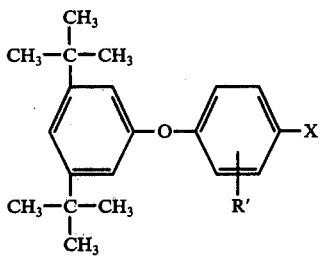

wherein R' and X are as defined in claim 1.

3. The composition in accordance with claim 2 in which the compound is 1-(3,5-di-tertiary butylphenoxy)-4-bromobenzene.

4. A method for treating lipidemia in mammals comprising administering to mammals in need of such treatment a hypolipidemic effective amount of a compound of the formula

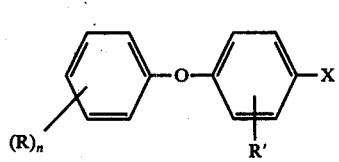

wherein R is branched alkyl of 3 to 5 carbon atoms,

R' is hydrogen or alkyl of 1 to 4 carbon atoms,

X is halo of atomic weight of from 18 to 80, and $n$ is 2, with the proviso that the R groups are not in ortho position with respect to each other.

5. A method in accordance with claim 4 in which the compound is administered in a daily amount of from 600 to 4000 milligrams.

6. A method in accordance with claim 4 in which the compound administered is a compound of the formula:

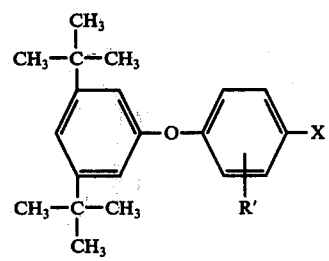

wherein R' and X are as defined in claim 4.

7. The method in accordance with claim 6 in which the compound administered is 1-(3,5-di-tertiary butylphenoxy)-4-bromobenzene.

8. A composition in accordance with claim 1 wherein X is bromo.

9. A method in accordance with claim 4 wherein X is bromo.

* * * * *